(12) United States Patent
Meriheinä

(10) Patent No.: US 7,962,309 B2
(45) Date of Patent: *Jun. 14, 2011

(54) METHOD AND DEVICE FOR MEASURING THE PROGRESS OF A MOVING PERSON

(75) Inventor: Ulf Meriheinä, Söderkulla (FI)

(73) Assignee: VTI Technologies Oy, Vantaa (FI)

( * ) Notice: Subject to any disclaimer, the term of this patent is extended or adjusted under 35 U.S.C. 154(b) by 430 days.

This patent is subject to a terminal disclaimer.

(21) Appl. No.: 12/000,998

(22) Filed: Dec. 19, 2007

(65) Prior Publication Data

US 2009/0018794 A1     Jan. 15, 2009

(30) Foreign Application Priority Data

Jul. 11, 2007 (FI) .................................. 20075536
Nov. 16, 2007 (FI) .................................. 20075817
Nov. 22, 2007 (FI) .................................. 20075830

(51) Int. Cl.
*G01P 15/00* (2006.01)

(52) U.S. Cl. ........ 702/141; 702/160; 702/176; 702/182; 702/189; 73/490; 73/514.01

(58) Field of Classification Search .................. 702/141, 702/160, 176, 182, 189; 73/490, 514.01
See application file for complete search history.

(56) References Cited

U.S. PATENT DOCUMENTS

| | | | |
|---|---|---|---|
| 4,578,769 A | 3/1986 | Frederick | |
| 5,583,776 A | 12/1996 | Levi et al. | |
| 5,955,667 A | 9/1999 | Fyfe | |
| 6,298,314 B1 | 10/2001 | Blackadar et al. | |
| 6,305,221 B1 * | 10/2001 | Hutchings | 73/488 |
| 6,356,856 B1 | 3/2002 | Damen et al. | |
| 7,092,846 B2 | 8/2006 | Vock et al. | |
| 2002/0040601 A1 | 4/2002 | Fyfe et al. | |
| 2003/0191582 A1 | 10/2003 | Terada | |
| 2004/0064286 A1 | 4/2004 | Levi et al. | |
| 2005/0021292 A1 | 1/2005 | Vock et al. | |
| 2007/0062279 A1 | 3/2007 | Chan et al. | |
| 2007/0067105 A1 | 3/2007 | Lee et al. | |
| 2007/0143068 A1 | 6/2007 | Pasolini et al. | |
| 2008/0255800 A1 * | 10/2008 | Meriheina et al. | 702/160 |

FOREIGN PATENT DOCUMENTS

| | | |
|---|---|---|
| CA | 2218242 C | 12/2005 |
| JP | 7-80115 | 3/1995 |
| WO | 0020874 A1 | 4/2000 |
| WO | WO 2005/004719 A1 | 1/2005 |
| WO | WO 2007/017471 A1 | 2/2007 |

OTHER PUBLICATIONS

International Search Report PCT/FI2008/050355 filed Jun. 13, 2008.

* cited by examiner

*Primary Examiner* — Sujoy K Kundu
(74) *Attorney, Agent, or Firm* — Squire, Sanders & Dempsey (US) LLP (57) ABSTRACT

The invention relates to measuring devices to be used in physical measuring, and more particularly, to a method and a device for measuring the progress of a moving person. In the solution according to the invention the quantities describing the progress of the moving person can be calculated based on vertical acceleration values of the body measured by means of an acceleration sensor, and on the measured time. The invention aims at providing a solution, better and simpler than prior solutions, for measuring the progress of a moving person, which solution is applicable for use in a multitude of measuring solutions for ways of locomotion of various types.

37 Claims, 2 Drawing Sheets

METHOD AND DEVICE FOR MEASURING THE PROGRESS OF A MOVING PERSON

FIELD OF THE INVENTION

The invention relates to measuring devices for use in physical measuring, and more specifically to a method and a device for measuring the progress of a moving person. The invention aims at providing a solution, better and simpler than prior ones, for measuring the progress of a moving person, which solution is applicable for use in a multitude of measuring solutions for different types of locomotion.

BACKGROUND OF THE INVENTION

In performing navigation based on inertia sensors, e.g. acceleration or angular velocity sensors, (inertia navigation), if the sensor signal is being integrated, it is important that the integration time is not extended too much, thus excessively increasing the error in position or direction caused by measuring errors of the sensor. In order to prevent that, the aim often is to divide the motion into periodically repetitive cycles of sufficient brevity. The method is called step-by-step navigation. In athletics coaching and competitions and in fitness exercise and other outdoor activities, such step-by-step navigation is important, wherein e.g. the speed of locomotion, the distance covered, the direction, the step rate (cadence), and the step time, as well as the step length are being measured. The way of locomotion could be e.g. running, walking, pole walking, competitive walking, cross-country skiing, downhill sports, roller skiing, skating or the like, where a cyclic motion is present.

Inertia navigation can work independently, or it can be used in combination with satellite navigation, in order to improve the accuracy of satellite navigation, particularly in areas of poor coverage of the satellite signal, for diagnostic purposes in satellite positioning error situations, or in order to reduce the power consumption of satellite navigation by means of increasing the intervals between instances of reception of the satellite signal.

In prior art, several solutions exist aiming at measuring the distance covered by using an acceleration sensor. In inertia navigation, for example, an acceleration sensor is most often used for measuring the distance covered. By means of the acceleration sensor, the contact time for the foot, i.e. the time during which the foot touches the ground, can be measured. For instance, the U.S. Pat. No. 4,578,769 discloses such a solution according to prior art. The method described in said Patent Publication provides good results for high running speeds, but it is not robust for slow running, nor for walking, where the event of the foot leaving the ground is hard to detect.

The acceleration sensor can be a simple switch or the like, which simply counts the number of steps and estimates the distance based on the number of steps, and the speed based on the cadence. These devices are called pedometers.

As a solution in a slightly more advanced system according to prior art, the actual motion of the walker can be measured at the foot by means of an acceleration sensor. Such solutions according to prior art are disclosed in e.g. the US Patent Application US 2002/0040601, the U.S. Pat. No. 5,955,667 and in the Canadian Patent Publication CA 2,218,242.

In the aforementioned patent publications, measuring signals from a multitude of acceleration sensors and angular motion sensors are combined, and significantly improved precision is achieved compared to the one for pedometers or contact time measurements. In these solutions according to prior art, the drawbacks, however, are the required number of sensors, a linear acceleration sensor as well as an angular motion sensor, for compensating the error caused by the earth's gravitational force, through the inclination and its variation, as well as the complexity of the algorithm, which manifest themselves in the size of the system, its costs, and power consumption.

In order to simplify the measuring system described above, a solution according to prior art has been disclosed, for using an acceleration sensor in such a way, that knowledge of the period of time the foot stays immobile, as it is on the ground, is being utilized and thus, the aim has been to improve the precision through automatic resetting. A solution according to prior art with such a technique is disclosed in e.g. U.S. Pat. No. 6,356,856. The method described in said Patent Publication suffers, however, from inaccuracy, when the inclination changes during the motion. Computing is complex in this case as well, and it requires power and program storage capacity.

One solution according to prior art, for detecting motion and for measuring the duration of movement is a disclosed method based on an acceleration sensor. Such a prior art solution is disclosed, for example, in the U.S. Pat. No. 6,298,314.

One further solution according to prior art, for a general device for measuring the movement of an athlete is disclosed, for example, in U.S. Pat. No. 7,092,846 and in the International Patent Application Publication WO 00/20874.

In literature, several solutions according to prior art, for step-by-step navigation have been disclosed. In all these known solutions, combining simplicity, and thereby low cost, small size, low power consumption and accuracy, is a problem. The major error sources for the presented solutions are the coupling of gravitation to the measuring signal as the angle changes, unambiguous detection of the contact between foot and ground, and foot slipping at ground contact, whereby the acceleration signal and the speed signal are distorted.

SUMMARY OF THE INVENTION

The object of the invention is an improved method and device for measuring the progress of a moving person. By means of the method and device according to this invention, a precision is achieved equaling that of the best methods presented above, but with an implementation solution of significantly reduced complexity, using one acceleration sensor without any inclination compensation. The sensor solution according to the invention is applicable for use in a multitude of solutions for measuring different types of locomotion.

According to a first aspect of the invention, a method is provided for measuring the progress of a moving person such, that at least one of the following quantities describing the progress of the moving person: speed, step rate, step count, step length, distance and way of locomotion, is calculated on the basis of vertical acceleration values of the body measured by means of an acceleration sensor, and on the basis of the measured time.

Preferably, step cycle-specific characteristic maximum accelerations $a_{max}$ falling within the positive half-cycle, i.e. during the acceleration stage, and correspondingly step cycle-specific characteristic minimum accelerations $a_{min}$ falling within the negative half-cycle, i.e. during the braking stage, are defined based on the measured values of vertical acceleration of the body.

Preferably, the step cycle-specific characteristic maximum acceleration values $a_{max}$ are obtained as the maxima of the step cycle-specific measured acceleration values and characteristic minimum accelerations $a_{min}$ are obtained as the minima of the step cycle-specific measured acceleration value.

Alternatively, the step cycle-specific characteristic maximum accelerations $a_{max}$ are obtained as the maxima for each step cycle of the analogically filtered acceleration sensor signals $a_{in}$ and characteristic minimum accelerations $a_{min}$ are obtained as the minima for each step cycle of the analogically filtered acceleration sensor signals $a_{in}$.

Further, alternatively, the step cycle-specific characteristic maximum accelerations $a_{max}$ are obtained as the maxima for each step cycle of the digitally filtered acceleration sensor signals $a_{in}$ and characteristic minimum accelerations $a_{min}$ are obtained as the minima for each step cycle of the digitally filtered acceleration sensor signals $a_{in}$.

Further, alternatively, the step cycle-specific characteristic maximum accelerations $a_{max}$ are obtained as the mean values for each step cycle of the digitally filtered acceleration sensor signals $a_{in}$ over times selected during the positive half-cycle and the step cycle-specific characteristic minimum accelerations $a_{min}$ are obtained as the mean values for each step cycle of the digitally filtered acceleration sensor signals $a_{in}$ over times selected during the negative half-cycle. Further, preferably, the function to be used in the digital filtering is:

$$a_{out} = a_{in}/\sqrt{[1+(f/f_0)^2]},$$

where f is the frequency and $f_0$ is a suitably selected boundary frequency.

Further, alternatively, the step cycle-specific characteristic maximum accelerations $a_{max}$ are obtained as the maxima for each step cycle of the signals $a_{in}$ from the acceleration sensor, filtered with digital weighting, and characteristic minimum accelerations $a_{min}$ are obtained as the minima for each step cycle of the signals $a_{in}$ from the acceleration sensor, filtered with digital weighting.

Further, alternatively, the step cycle-specific characteristic maximum accelerations $a_{max}$ are obtained as the mean values for each step cycle of the signals $a_{in}$ from the acceleration sensor filtered with digital weighting over times selected during the positive half-cycle and characteristic minimum accelerations $a_{min}$ are obtained as the mean values for each step cycle of the signals $a_{in}$ from the acceleration sensor filtered with digital weighting over times selected during the negative half-cycle.

Preferably, the function to be used in the digital weighted filtering is:

$$a_{out}(n) = (1-k)*a_{out}(n-1) + a_{in}*k,$$

where n indicates the n:th sample and k is the weighting factor.

Preferably, the speed v is calculated based on the characteristic maximum accelerations $a_{max}$ of the vertical acceleration as follows:

$$v \approx k \cdot \left( \frac{\frac{a_{max}}{1g} + 1}{T_{step}} - f_0 \right),$$

where g is the acceleration caused by gravitation, $f_{ref}$ is a reference frequency and the characteristic maximum acceleration $a_{max}$ is the maximum value of the vertical acceleration filtered at a suitably selected boundary frequency $f_0$. Alternatively, the speed v is calculated based on the characteristic minimum accelerations $a_{min}$ of the vertical acceleration as follows:

$$v \approx k \cdot \sqrt{|a_{min}|}.$$

Preferably, in calculating the quantities describing the progress of the moving person, the time $T_{step}$ used up for one step is obtained as the time interval between two equivalent points, such as a maximum, a minimum, or a point of exceeding or falling below a certain value, on the acceleration graph derived from the measured values of the vertical acceleration.

Preferably, the step length $s_{step}$ is calculated using the formula:

$$s_{step} = v*T_{step}.$$

Preferably, the step rate $f_{step}$ is calculated using the formula:

$$f_{step} = 1/T_{step}.$$

Further, preferably, the step count n is calculated on the basis of the number n of equivalent points, such a maximum, a minimum, or a point of exceeding or falling below a certain value, on the acceleration graph given by the measured values of vertical acceleration.

Further, preferably, the distance covered s is calculated as the sum of the step lengths:

$$s = \sum_{i=1}^{n} s_{step}(i).$$

Preferably, the method distinguishes between ways of progress, like walking, running, and skiing, based on acceleration maximum and minimum, the characteristic maximum and minimum acceleration values $a_{max}$ and $a_{min}$ and/or the step rate. Preferably, the method makes an individual calibration for each way of progress, like running, walking, pole walking, or cross-country skiing. Preferably, the method is adapted for use in step-by-step navigation.

According to a second aspect of the invention, a device is provided for measuring the progress of a moving person such, that the device is adapted to measure a minimum acceleration and time such, that at least one of the following quantities describing the progress of the moving person: speed, step rate, step count, step length, distance and way of progress, is calculated based on the values of vertical acceleration of the body measured by means of an acceleration sensor, and on the measured time.

Preferably, the device is adapted to determine step cycle-specific characteristic maximum accelerations $a_{max}$ falling within the positive half-cycle, i.e. during the acceleration stage, and, correspondingly, step cycle-specific characteristic minimum accelerations $a_{min}$ falling within the negative half-cycle, i.e. during the braking stage, based on the measured values of vertical acceleration of the body.

Preferably, the device is adapted to determine the step cycle-specific characteristic maximum accelerations $a_{max}$ as the maxima of the step cycle-specific measured acceleration values and characteristic minimum acceleration values $a_{min}$ as the minima of the step cycle-specific measured acceleration values.

Alternatively, the device is adapted to determine the step cycle-specific characteristic maximum accelerations $a_{max}$ as the maxima for each step cycle of the analogically filtered acceleration sensor signals $a_{in}$ and characteristic minimum accelerations $a_{min}$ as the minima for each step cycle of the analogically filtered acceleration sensor signals $a_{in}$.

Further, alternatively, the device is adapted to determine the step cycle-specific characteristic maximum accelerations $a_{max}$ as the maxima for each step cycle of the digitally filtered acceleration sensor signals $a_{in}$ and characteristic minimum accelerations $a_{min}$ as the minima for each step cycle of the digitally filtered acceleration sensor signals $a_{in}$.

Further, alternatively, the device is adapted to determine the step cycle-specific characteristic maximum accelerations $a_{max}$ as the mean values for each step cycle of the digitally filtered acceleration sensor signals $a_{in}$ over times selected during the positive half-cycle and characteristic minimum accelerations $a_{min}$ as the mean values for each step cycle of the digitally filtered acceleration sensor signals $a_{in}$ over times selected during the negative half-cycle. Further, preferably, the device is adapted to use, in the digital filtering, the function:

$$a_{out}=a_{in}/\sqrt{[1+(f/f_0)^2]},$$

where f is the frequency and $f_0$ is a suitably selected boundary frequency.

Further, alternatively, the device is adapted to determine the step cycle-specific characteristic maximum accelerations $a_{max}$ as the maxima for each step cycle of the signals $a_{in}$ from the acceleration sensor, filtered with digital weighting, and characteristic minimum accelerations $a_{min}$ as the minima for each step cycle of the signals $a_{in}$ from the acceleration sensor, filtered with digital weighting.

Further, alternatively, the device is adapted to determine the step cycle-specific characteristic maximum accelerations $a_{max}$ as the mean values for each step cycle of the signals $a_{in}$ from the acceleration sensor filtered with digital weighting over times selected during the positive half-cycle and characteristic minimum accelerations $a_{min}$ as the mean values for each step cycle of the signals $a_{in}$ from the acceleration sensor filtered with digital weighting over times selected during the negative half-cycle. Further, preferably, the device is adapted in the digital weighted filtering to use the function:

$$a_{out}(n)=(1-k)*a_{out}(n-1)+a_{in}*k,$$

where n indicates the n:th sample and k is the weighting factor.

Preferably, the device is adapted to calculate the speed v based on the characteristic maximum accelerations $a_{max}$ of the vertical acceleration as follows:

$$v \approx k \cdot \left( \frac{\frac{a_{max}}{1g}+1}{T_{step}} - f_0 \right),$$

where g is the acceleration caused by gravitation, $f_{ref}$ is a reference frequency and the characteristic maximum acceleration $a_{max}$ is the maximum value of the vertical acceleration filtered at a suitably selected boundary frequency $f_0$. Alternatively, the speed v is calculated based on the characteristic minimum accelerations $a_{min}$ of the vertical acceleration as follows:

$$v \approx k \cdot \sqrt{|a_{min}|}.$$

Preferably, the device is adapted, in calculating the quantities describing the progress of a moving person, to determine the time $T_{step}$ used up for one step as the time interval between two equivalent points, such as a maximum, a minimum, or a point of exceeding or falling below a certain value, on the acceleration graph derived from the measured values of the vertical acceleration.

Preferably, the device is adapted to calculate the step length $s_{step}$ using the formula:

$$s_{step}=v*T_{step}.$$

Preferably, the device is adapted to calculate the step rate $f_{step}$ using the formula:

$$f_{step}=1/T_{step}.$$

Further, preferably, the device is adapted to calculate the step count n on the basis of the number n of equivalent points, such a maximum, a minimum, or a point of exceeding or falling below a certain value, on the acceleration graph given by the measured values of vertical acceleration.

Further, preferably, the device is adapted to calculate the distance covered s as the sum of the step lengths:

$$s = \sum_{i=1}^{n} s_{step}(i).$$

Preferably, the device is adapted to distinguish between ways of progress, like walking, running, and skiing, based on acceleration maximum and minimum, the characteristic maximum and minimum acceleration values $a_{max}$ and $a_{min}$ and/or the step rate.

Preferably, the device is adapted to make an individual calibration for each way of progress, like running, walking, pole walking, or cross-country skiing.

Preferably, the device is adapted for use in step-by-step navigation. Further, preferably, the device is adapted to cooperate with an altimeter, satellite navigation devices, and/or a magnetometer. Further, preferably, the device is adapted to receive and/or utilize map data base data and/or terrain inclination data.

According to a third aspect of the invention, a device to be positioned at the middle of the body of the moving person is provided, such that the device comprises a device, as described above, for measuring the progress of a moving person. Preferably, the device to be positioned at the middle of the body the moving person is positioned at a piece of clothing, a piece of headwear, the neck, a pocket, or the belt of the moving person.

According to a fourth aspect of the invention, a display unit for a moving person is provided such, that the display unit for the moving person is adapted to cooperate with a device, as described above, measuring the progress of the moving person.

According to a fifth aspect of the invention, a system for measuring the progress of a moving person is provided, such that the system comprises a device, as described above, for measuring the progress of the moving person, and, adapted to cooperate with this device, a display unit for the moving person. Preferably, said device for measuring the progress of the moving person and said display unit for the moving person are integrated in one device.

BRIEF DESCRIPTION OF THE DRAWINGS

Below, the invention and its preferred embodiments are described in detail with exemplary reference to the enclosed figures, of which.

DETAILED DESCRIPTION OF THE INVENTION

Figure 1:
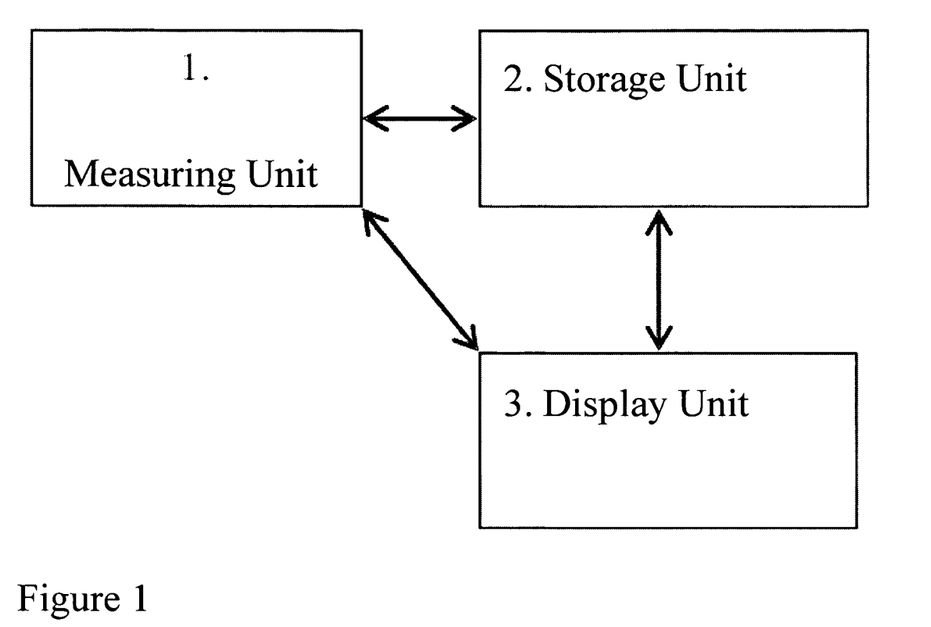
FIG. 1 shows a diagram of a measuring apparatus according to the invention.

FIG. 1 shows a diagram of a measuring apparatus according to the invention. The apparatus can consist of a measuring unit 1, a storage unit 2 and a display unit 3. These communicate with each other using wireless or wired connections. Some of the units, or all of them, can be integrated in the same casing or unit. The measuring unit is attached close to the human body, e.g. close to the middle. The measuring unit is typically positioned at some garment of the moving person, like e.g. a piece of clothing, a piece of headwear, the neck, a pocket, or close to the middle, i.e. close to the body's center of gravity, e.g. at the belt. The display unit is typically located in a clearly visible position. It can be integrated, for example, in a measuring and storage unit, or it can be separate. It can also be part of a watch, a satellite navigator, a mobile terminal, a radio receiver, a player, or the like. Any calibration data for the measuring device are stored in one unit or in several units.

Figure 2:
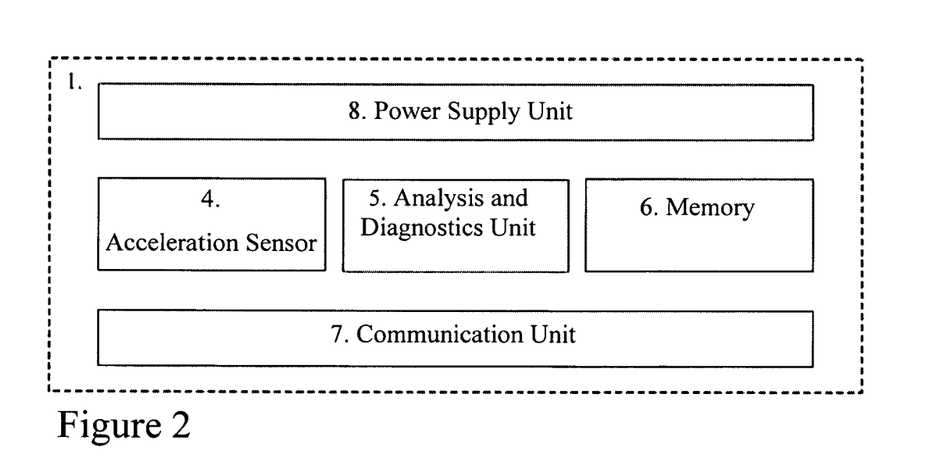
FIG. 2 shows a view of a measuring unit according to the invention.

FIG. 2 shows a view of a measuring unit according to the invention. The measuring unit 1 can comprise an acceleration sensor 4 of 1 to 3 axes, a unit 5 for analysis and diagnostics of the acceleration data, a volatile and a nonvolatile memory 6, a communication unit 7, and a power supply 8, e.g. a battery, an accumulator, a harvester or some similar device. The analysis unit can, for example, be based on a microprocessor or a DSP (Digital Signal Processor). The memory stores, for instance, user data, calibration data, measurement data and other log data. The communication unit comprises, for example, a transfer protocol generator, a required interface, or a radio transmitter, a receiver and an antenna.

The measuring unit can be positioned fastened close to the human body, like, for example, close to the middle, i.e. close to the body's center of gravity. The measuring unit is, typically, positioned at the clothing of the moving person, like, for instance, a piece of clothing, a piece of headwear, the neck, a pocket, or the belt.

Figure 3:
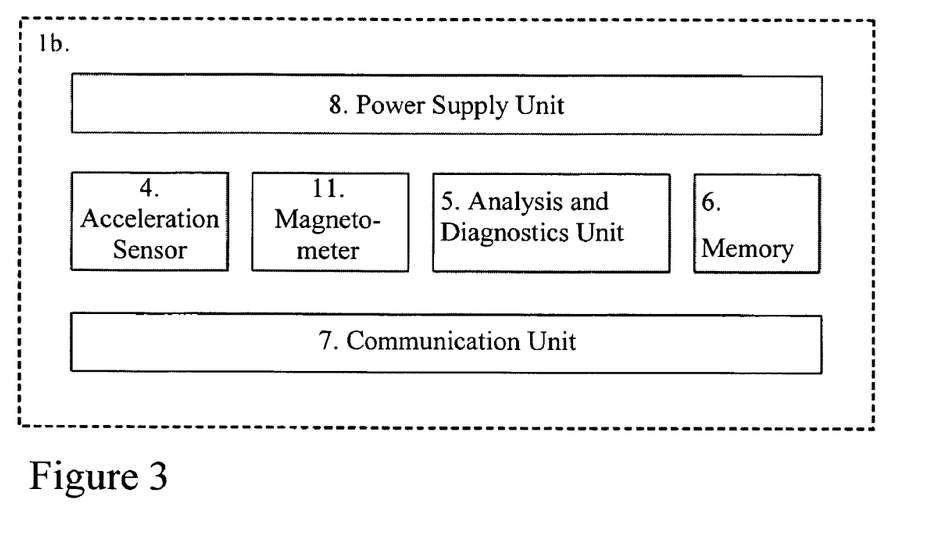
FIG. 3 shows a view of an alternative measuring unit according to the invention.

FIG. 3 shows a view of an alternative measuring unit according to the invention. If, in addition to the speed and the distance covered, one wants to know the traveled route, a magnetometer 11 of 2 or 3 axes can be added to the alternative measuring unit for the compass direction to be determined for each step, or once in a while.

In the solution according to the invention, the acceleration of the cyclic motion of progress is being measured in one or more directions. From the vertical acceleration values measured during each step cycle, a characteristic maximum acceleration $a_{max}$ occurring during the positive half cycle or the acceleration stage and, respectively, a characteristic minimum acceleration $a_{min}$ occurring during the negative half cycle or the braking stage are being determined.

As values of the characteristic maximum acceleration $a_{max}$ and the characteristic minimum acceleration $a_{min}$ accelerations are defined, that clearly differ from zero, whereby the influence of the zero point error in the acceleration sensor or of the coupling of gravitation, caused by inclination, on the metering signal is minimal, since they are clearly lower than the values $a_{max}$ and $a_{min}$.

In the solution according to the invention, the characteristic maximum acceleration $a_{max}$ and the characteristic minimum acceleration $a_{min}$ can be defined, for example, directly as the maximum and/or the minimum of the vertical acceleration value from the raw data measured by the acceleration sensor. Alternatively, in the solution according to the invention, the values $a_{max}$ and $a_{min}$ can be defined by filtering the acceleration sensor signal $a_{in}$ analogically by, for example, mechanical damping of the signal $a_{in}$.

Further, alternatively, in a solution according to the invention, the values $a_{max}$ and $a_{min}$ can be defined by filtering the acceleration sensor signal $a_{in}$ digitally, by means of, for example, an RC filter. In this case, in the digital filtering, the function used in the first stage filtering could be, for instance:

$$a_{out}=a_{in}/\sqrt{[1+(f/f_0)^2]},$$

where f=frequency and $f_0$=the boundary frequency for −3 dB and the values $a_{max}$ and $a_{min}$ can be defined based on this filtered signal as, for example, the maximum and/or the minimum of the filtered acceleration value.

Further, alternatively, in the solution according to the invention, the values $a_{max}$ and $a_{min}$ can be defined by filtering the acceleration sensor signal $a_{in}$ by means of digital weighting. Here, the function to be used in the digital weighting could be, for instance:

$$a_{out}(n)=(1-k)*a_{out}(n-1)+a_{in}*k,$$

where n indicates the n:th sample and k is the weighting factor.

Further, alternatively, in a solution according to the invention, the values $a_{max}$ and $a_{min}$ can be defined by using a mean value calculated from the measured acceleration value over times selected during the positive and/or the negative half cycle.

The time used up for one step $T_{step}$ is obtained as the time interval between two equivalent points, such a maximum, a minimum, or a point of exceeding or falling below a certain value, on the acceleration graph given by the measured values of vertical acceleration. The time $T_C$ spent in ground contact during a step is obtained based on the length of time of zero acceleration in the acceleration graph derived from the measured vertical acceleration values.

For running, it has been noted that the speed is proportional to the inverse of the contact time and to the force produced in the take off. Since the average vertical acceleration of the body is zero, $$T_C \cdot a_{max}+(T_{step}-T_C)\cdot a_{min}=0,$$

the speed of locomotion v is obtained based on the characteristic maximum acceleration $a_{max}$, in other words, $$v \approx k \cdot \left( \frac{\frac{a_{max}}{1g}+1}{T_{step}} - f_0 \right),$$

where g is the acceleration caused by gravitation, $f_{ref}$ is a reference frequency and the characteristic maximum acceleration $a_{max}$ is the maximum value of the vertical acceleration strongly filtered at, for instance, the boundary frequency $f_0$=6 Hz. In running, the characteristic maximum acceleration $a_{max}$ of the middle or some other part of the body is a good measure of the speed of progress.

For walking, the speed is obtained based on the characteristic minimum acceleration $a_{min}$ of the vertical acceleration, in other words, $$v \approx k \cdot \sqrt{|a_{min}|}.$$

The factors k depend, to some extent, on the boundary frequency in the filtering of the acceleration data. In walking, the characteristic minimum acceleration $a_{min}$ of the middle or some other part of the body is a good measure of the speed of progress.

In the solution according to the invention, the step length $s_{step}$ can be calculated using the formula:

$$s_{step}=v*T_{step},$$

and, correspondingly, the step rate or the cadence $f_{step}$ can be calculated using the formula:

$$f_{step}=1/T_{step}.$$

In the solution according to the invention, running and walking can be distinguished from each other based on step rate and speed of progress. At low running speeds, a non-linear model can be used, and running and walking can be adapted to each other.

In the solution according to the invention, the step count n can be calculated on the basis of the number n of equivalent points, such a maximum, a minimum, or a point of exceeding or falling below a certain value, on the acceleration graph given by the measured values of vertical acceleration. Further, in the solution according to the invention, the distance covered s can be calculated as the sum of the step lengths:

$$s = \sum_{i=1}^{n} s_{step}(i).$$

In the solution according to the invention, a single acceleration sensor of one axis can be used, and thus, implementing the calculations of the formulae presented above is a simple task by means of, for example, a microcontroller. This enables a small, low cost, and low power sensor solution, by means of which a precision sufficient for consumer products is achieved. Without individual calibration, the relative error, at distances exceeding one kilometer, is less than 10%.

In the solution according to the invention, an acceleration sensor of many axes can be used as well, and that enables, for example, diagnosing stationary running.

In the solution according to the invention, a magnetometer of two axes can also be used, by means of which the length and direction of every step can be obtained. There will be inclination compensation as well, since the inclination of the body is more or less constant. Calibration of direction and speed can be done by running a straight line back and forth.

In the solution according to the invention, the speed estimate suffers a minimal impact from the zero point error in the acceleration sensor or from gravitation coupling into the metering signal caused by inclination, when using the characteristic maximum acceleration $a_{max}$ and the characteristic minimum acceleration $a_{min}$, which values are large numbers in comparison with those. The ways of progress, e.g. walking, running, and skiing, can be distinguished from each other based on the characteristic maximum acceleration $a_{max}$, the characteristic minimum acceleration $a_{min}$, and/or the step rate.

In the solution according to the invention, based on the acceleration values measured during the step cycles, characteristic maximum acceleration and characteristic minimum acceleration values $a_{max}$ and $a_{min}$ for each step cycle are defined, by means of which values the speed, the step rate, the step length, and the distance can be calculated with low power consumption using simple arithmetic, for example by using a polynome.

The system, even if not calibrated, provides good precision. In order to improve precision, individual calibration can be made for different modes of progress, e.g. running, walking, pole walking, or cross-country skiing. This can be done over a known distance using one speed or a multitude of speeds. By repeating the calibration, errors in speed and distance caused by stochastic errors are reduced, whereby precision is further improved. New calibration data can be added to the old data by suitable digital filtering. In addition, for further improvement of the precision, information about the characteristic maximum and minimum acceleration values $a_{max}$ and $a_{min}$ can be combined with contact time data, with change in altitude and terrain inclination data obtained from an altimeter, and/or with satellite navigation.

A complete step-by-step navigation unit is provided by adding to the step data the compass direction obtained from a magnetometer. The magnetometer can be calibrated, e.g. by rotating about a vertical axis. A direction error in the installation can be calibrated away by, e.g. walking a selected calibration route back and forth. Absolute coordinate data is obtained by combining this navigation unit with satellite navigation. Precision is further improved by combining the navigation unit with a map database and with an altimeter, since plausibility checks of the coordinates and movement can be made based on the altitude and changes in altitude.

By using an acceleration sensor signal perpendicular to the principal metering direction, a measure of the efficiency of locomotion is obtained.

In the solution according to the invention, characteristic maximum acceleration and characteristic minimum acceleration values $a_{max}$ and $a_{min}$ and/or maximum and/or minimum acceleration values obtained from an acceleration sensor of one or more axes can be used for estimating the speed of progress of a person. The signal of the acceleration sensor can be suitably filtered by means of mechanical, electronic, analog and/or digital filtering such, that the speed estimate is as exact and reliable as possible. In the solution according to the invention, step time, step rate, step length, and distance accumulated from the steps can be calculated based on the speed and the time interval between consecutive maxima or minima.

In the solution according to the invention, walking, running, and skiing, or some other way of progress can be distinguished from each other based on, for example, the maximum and minimum acceleration of the middle of the body, the characteristic maximum and minimum acceleration values $a_{max}$ and $a_{min}$ and/or the step rate.

In the solution according to the invention, the parameters for an average person running and walking can be utilized without individual calibration of the measuring system. The measuring system can be calibrated by means of individual calibration for one speed or for a multitude of speeds for a certain way of progress, e.g. running or walking. In the solution according to the invention, the calibration of the measuring system can be repeated such, that new data is combined with the old data by digital filtering. The precision of the measuring system can be improved by combining contact time data with the maximum and minimum acceleration data.

In the solution according to the invention, the direction of each step or the direction of the distance covered observed from time to time can be determined by combining the speed estimate with the compass direction obtained from a magnetometer of 2 or 3 axes. A magnetometer and an installation direction error can be compensated for by rotating about a vertical axis and by walking a selected calibration route back and forth.

In the solution according to the invention, the efficiency of the locomotion can be estimated by combining with the characteristic maximum acceleration values and the characteristic minimum acceleration values $a_{max}$ and $a_{min}$ and/or with the maximum and minimum acceleration value data, acceleration values measured at right angles to those.

By means of the method and device according to the invention, a precision is achieved equal to that of the best methods presented above, by an implementation solution of significantly greater simplicity, utilizing one acceleration sensor without inclination compensation.

By means of the method and device according to the invention, the complicated algorithms of prior systems are avoided, and low cost, low power consumption, and small size are achieved.

The low power consumption of the method and device according to the invention allows a small battery and gives it long life, or even a battery-free solution based on, for example, recovery of the kinetic energy occurring in the measuring device (harvesting).

The simple measuring algorithm of the method and device according to the invention allows the computations to be performed entirely in the measuring unit, which reduces the need for data transfer from the measuring unit, and thus, the power consumption of data transmission utilizing radio traffic.

The small size of the measuring unit of the solution according to the invention allows the unit to be positioned, for example, at a piece of garment of the moving person, like, for example a piece of clothing, a piece of headwear, the neck, a pocket or close to the middle of the body, i.e. near the center of gravity of the body, at the belt, for instance. The method according to the invention is applicable, for example, to both slow and fast running, to walking at various speeds, pole walking, cross-country skiing, downhill sports, roller skiing, roller-skating and skating.

The method and device according to the invention can be used for measuring a moving person's speed, the step length, and the distance covered, based on maximum and minimum acceleration values of the body, given by an acceleration sensor of one axis for vertical acceleration and/or characteristic maximum and minimum acceleration values $a_{max}$ and $a_{min}$. In the solution according to the invention, the acceleration signal can be optimally filtered such, that the acceleration signal gives as good a picture of the speed as possible.

In the solution according to the invention, the ways of locomotion of the moving person, like walking and running, can be distinguished from each other based on the cadence and the speed of locomotion. In the solution according to the invention the parameters for an average person walking and running can be utilized without any individual calibration of the measuring system. The solution according to the invention enables calibration of the single point measuring system for walking and for running.

The solution according to the invention enables diagnosing stationary running by means of a sensor of longitudinal acceleration. The solution according to the invention enables the direction of each step and the distance covered to be determined by means of a compass of two or three axes. The solution according to the invention enables calibration of the installation error of the compass by traveling the same route back and forth.

The invention claimed is:

1. A method for measuring the progress of a moving person, the method comprising:
    calculating at least one of the following quantities describing the progress of the moving person: speed, step rate, step count, step length, distance and way of progress, based on values of a vertical acceleration of a body of the moving person measured by an acceleration sensor over a measured time;
    defining step cycle-specific characteristic maximum accelerations $a_{max}$ falling within a positive half-cycle, during an acceleration stage, and correspondingly step cycle-specific characteristic minimum accelerations $a_{min}$ falling within a negative half-cycle during a braking stage, based on measured values of the vertical acceleration of the body of the moving person; and
    defining the step cycle-specific characteristic maximum acceleration values $a_{max}$ mean values for each step cycle of digitally filtered acceleration sensor signals $a_{in}$ over times selected during the positive half-cycle and the step cycle-specific characteristic minimum accelerations $a_{min}$ as mean values for each step cycle of the digitally filtered acceleration sensor signals $a_{in}$ over times selected during the negative half-cycle.

2. The method according to claim 1, wherein the determining comprises using a function for the digital filtering, wherein the function is:

$$a_{out}=a_{in}/\sqrt{[1+(f/f_0)^2]},$$

where f is the frequency and $f_0$ is a suitably selected boundary frequency.

3. The method according to claim 1, further comprising:
    defining the step cycle-specific characteristic maximum accelerations $a_{max}$ as maxima for each step cycle of the signals $a_{in}$ from the acceleration sensor filtered with digital weighting; and
    defining the step cycle-specific characteristic minimum accelerations $a_{min}$ as minima for each step cycle of the signals $a_{in}$ from the acceleration sensor filtered with digital weighting.

4. The method according to claim 1, further comprising:
    defining the step cycle-specific characteristic maximum accelerations $a_{max}$ as mean values for each step cycle of the signals $a_{in}$ from the acceleration sensor filtered with digital weighting over times selected during the positive half-cycle; and
    defining the step cycle-specific characteristic minimum accelerations $a_{min}$ as mean values for each step cycle of the signals $a_{in}$ from the acceleration sensor filtered with digital weighting over times selected during the negative half-cycle.

5. The method according to claim 3, wherein a function used in the digital weighted filtering is:

$$a_{out}(n)=(1-k)*a_{out}(n-1)+a_{in}*k,$$

where n indicates the n:th sample and k is the weighting factor.

6. The method according to claim 1, wherein the calculating comprises calculating the speed v based on the step cycle-specific characteristic maximum acceleration values $a_{max}$ of the vertical acceleration as follows:

$$v \approx k \cdot \left( \frac{\frac{a_{max}}{1g}+1}{T_{step}} - f_0 \right),$$

where g is an acceleration caused by gravitation, $f_{ref}$ is a reference frequency and the step cycle-specific characteristic maximum acceleration $a_{max}$ is a maximum value of the vertical acceleration filtered at a suitably selected boundary frequency $f_0$.

7. The method according to claim 1, wherein the calculating comprises calculating the speed v based on the step cycle-specific characteristic minimum accelerations $a_{min}$ of the vertical acceleration as follows:

$$v \approx k \cdot \sqrt{|a_{min}|}.$$

8. The method according to claim 1, wherein the calculating comprises obtaining a time $T_{step}$ used up for one step as a time interval between two equivalent points, such as a maximum, a minimum, or a point of exceeding or falling below a certain value, on an acceleration graph derived from the measured values of the vertical acceleration.

9. The method according to claim 8, further comprising:
    calculating the step length $s_{step}$ using the formula:

$$s_{step}=v*T_{step}.$$

10. The method according to claim 8, further comprising: calculating the step rate $f_{step}$ using the formula:

$$f_{step}=1/T_{step}.$$

11. The method according to claim 8, further comprising: calculating the step count n based on a number n of equivalent points, such as a maximum, a minimum, or a point of exceeding or falling below a certain value, on the acceleration graph given by the measured values of vertical acceleration.

12. The method according to claim 8, further comprising: calculating the distance covered s as a sum of the lengths of the steps:

$$s = \sum_{i=1}^{n} s_{step}(i).$$

13. The method according to claim 1, wherein the calculating comprises distinguishing between ways of progress selected from one of walking, running, and skiing, based on acceleration maximum and minimum, the step cycle-specific characteristic maximum and minimum acceleration values $a_{max}$ and $a_{min}$ and/or the step rate.

14. The method according to claim 13, wherein the calculating comprises making an individual calibration for each way of progress selected from one of running, walking, pole walking, or cross-country skiing.

15. The method according to claim 1, wherein the method is adapted for use in step-by-step navigation.

16. A device for measuring the progress of a moving person, the device being configured to
measure a minimum acceleration and time such, that at least one of the following quantities describing the progress of the moving person: speed, step rate, step count, step length, distance and way of locomotion, is calculated based on values of a vertical acceleration of a body of the moving person measured by an acceleration sensor over a measured time;
determine step cycle-specific characteristic maximum accelerations $a_{max}$ falling within a positive half-cycle, during an acceleration stage, and correspondingly, step cycle-specific characteristic minimum accelerations $a_{max}$ falling within a negative half-cycle, during a braking stage, based on measured values of the vertical acceleration of the body of the moving person; and
determine the step cycle-specific characteristic maximum accelerations $a_{max}$ as mean values for each step cycle of digitally filtered acceleration sensor signals $a_{in}$ over times selected during the positive half-cycle and the step cycle-specific characteristic minimum accelerations $a_{min}$ as mean values for each step cycle of the digitally filtered acceleration sensor signals $a_{in}$ over times selected during the negative half-cycle.

17. The device according to claim 16, wherein the device is configured to use, in the digital filtering, the function:

$$a_{out}=a_{in}/\sqrt{[1+(f/f_0)^2]},$$

where f is the frequency and $f_0$ is a suitably selected boundary frequency.

18. The device according to claim 16, wherein the device is configured to
determine the step cycle-specific characteristic maximum accelerations $a_{max}$ as maxima for each step cycle of the signals $a_{in}$ from the acceleration sensor filtered with digital weighting, and
determine the step cycle-specific characteristic minimum accelerations $a_{min}$ as minima for each step cycle of the signals $a_{in}$ from the acceleration sensor filtered with digital weighting.

19. The device according to claim 16, wherein the device is configured to
determine the step cycle-specific characteristic maximum accelerations $a_{max}$ as mean values for each step cycle of the signals $a_{in}$ from the acceleration sensor filtered with digital weighting over times selected during the positive half-cycle; and
determine the step cycle-specific characteristic minimum accelerations $a_{min}$ as mean values for each step cycle of the signals $a_{in}$ from the acceleration sensor filtered with digital weighting over times selected during the negative half-cycle.

20. The device according to claim 18, wherein the device is configured to use, in the digital weighted filtering, the function:

$$a_{out}(n)=(1-k)*a_{out}(n-1)+a_{in}*k,$$

where n indicates the n:th sample and k is the weighting factor.

21. The device according to claim 16, wherein the device is configured to calculate the speed v based on the step cycle-specific characteristic maximum accelerations $a_{max}$ of the vertical acceleration as follows:

$$v \approx k \cdot \left( \frac{\frac{a_{max}}{1g}+1}{T_{step}} - f_0 \right),$$

where g is an acceleration caused by gravitation, $f_{ref}$ is a reference frequency and the step cycle-specific characteristic maximum acceleration $a_{max}$ is a maximum value of the vertical acceleration filtered at a suitably selected boundary frequency $f_0$.

22. The device according to claim 16, wherein the device is configured to calculate the speed v based on the step cycle-specific characteristic minimum accelerations $a_{min}$ of the vertical acceleration as follows:

$$v \approx k \cdot \sqrt{|a_{min}|}.$$

23. The device according to claim 16, wherein the device is configured, in calculating the quantities describing the progress of the moving person, to determine the time $T_{step}$ used up for one step as a time interval between two equivalent points, such as a maximum, a minimum, or a point of exceeding or falling below a certain value, on an acceleration graph derived from the measured values of the vertical acceleration.

24. The device according to claim 23, wherein the device is configured to calculate the step length $s_{step}$ using the formula:

$$s_{step}=v*T_{step}.$$

25. The device according to claim 23, wherein the device is configured to calculate the step rate $f_{step}$ using the formula:

$$f_{step}=1/T_{step}.$$

26. The device according to claim 23, wherein the device is configured to calculate the step count n based on a number n of equivalent points, such as a maximum, a minimum, or a point of exceeding or falling below a certain value, on the acceleration graph given by the measured values of vertical acceleration.

27. The device according to claim 23, wherein the device is configured to calculate the distance covered s as a sum of the step lengths:

$$s = \sum_{i=1}^{n} s_{step}(i).$$

28. The device according to claim 16, wherein the device is configured to distinguish between ways of progress, selected from one of walking, running, and skiing, based on acceleration maximum and minimum, the step cycle-specific characteristic maximum and minimum acceleration values $a_{max}$ and $a_{min}$ and/or the step rate.

29. The device according to claim 28, wherein the device is configured to make an individual calibration for each way of progress, selected from one of running, walking, pole walking, or cross-country skiing.

30. The device according to claim 16, wherein the device is configured for use in step-by-step navigation.

31. The device according to claim 30, wherein the device is configured to cooperate with an altimeter, satellite navigation devices, and/or a magnetometer.

32. The device according to claim 30, wherein the device is configured to receive and/or utilize map database data and/or terrain inclination data.

33. A device configured to be positioned at a middle of a body of a moving person, wherein the device comprises a device according to claim 16 for measuring the progress of the moving person.

34. The device according to claim 33, wherein the device configured to be positioned at the middle of the body of the moving person can be configured to a piece of clothing, a piece of headwear, the neck, a pocket, or a belt of the moving person.

35. A display unit for a moving person, wherein the display unit for the moving person is configured to cooperate with a device according to claim 16 measuring the progress of a moving person.

36. A system for measuring a progress of a moving person, wherein the system comprises a device according to claim 16 for measuring the progress of the moving person, and a display unit for the moving person that is configured to cooperate with the device.

37. The system according to claim 36, wherein the device for measuring the progress of the moving person and the display unit for the moving person are integrated in one device.

* * * * *